United States Patent
Shin et al.

(10) Patent No.: US 8,491,489 B2
(45) Date of Patent: Jul. 23, 2013

(54) SYSTEM, MEDIUM, AND METHOD TO CONDUCE A USER'S BREATHING

(75) Inventors: Sang Hoon Shin, Seongnam-si (KR); Sun Gi Hong, Hwaseong-si (KR); Kyung Ho Kim, Yongin-si (KR); Wan Taek Han, Hwaseong-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 1449 days.

(21) Appl. No.: 11/603,015

(22) Filed: Nov. 22, 2006

(65) Prior Publication Data
US 2007/0167855 A1    Jul. 19, 2007

(30) Foreign Application Priority Data
Jan. 4, 2006 (KR) .................. 10-2006-0001104

(51) Int. Cl.
*A61B 5/08* (2006.01)
(52) U.S. Cl.
USPC .......................................... 600/529; 600/538
(58) Field of Classification Search
USPC ......................................................... 600/529
See application file for complete search history.

(56) References Cited

U.S. PATENT DOCUMENTS

| | | | | |
|---|---|---|---|---|
| 6,162,183 | A * | 12/2000 | Hoover | 600/534 |
| 6,168,568 | B1 * | 1/2001 | Gavriely | 600/529 |
| 6,287,264 | B1 * | 9/2001 | Hoffman | 600/538 |
| 6,858,182 | B1 | 2/2005 | Ito et al. | |
| 2005/0053523 | A1 | 3/2005 | Brooke | |
| 2007/0093723 | A1 * | 4/2007 | Keall et al. | 600/534 |

FOREIGN PATENT DOCUMENTS

| | | |
|---|---|---|
| JP | 2000-341375 | 12/2000 |
| JP | 2001-309430 | 11/2001 |
| JP | 2002-044007 | 2/2002 |
| KR | 20-1996-009562 | 3/1996 |
| KR | 1996-0009562 | 3/1996 |
| KR | 10-2002-0029054 | 4/2002 |
| KR | 10-2002-0085050 | 11/2002 |
| KR | 10-2003-0018953 | 3/2003 |
| KR | 10-2004-0081626 | 9/2004 |

* cited by examiner

*Primary Examiner* — Patricia Mallari
*Assistant Examiner* — Michael R Bloch
(74) *Attorney, Agent, or Firm* — Staas & Halsey LLP

(57) ABSTRACT

A system, medium, and method conducing a user's breathing, in which a sound generated during a user's exhale and/or an ambient temperature change occurring during the exhale is sensed to measure a respiratory waveform of the user. Respiratory information of the user may then be produced from the respiratory waveform, and when the respiratory information of the user is different from normal respiratory information of the user, breathing information according to the normal respiratory information may be provided to the user so the user can use the same to modify their breathing.

14 Claims, 7 Drawing Sheets

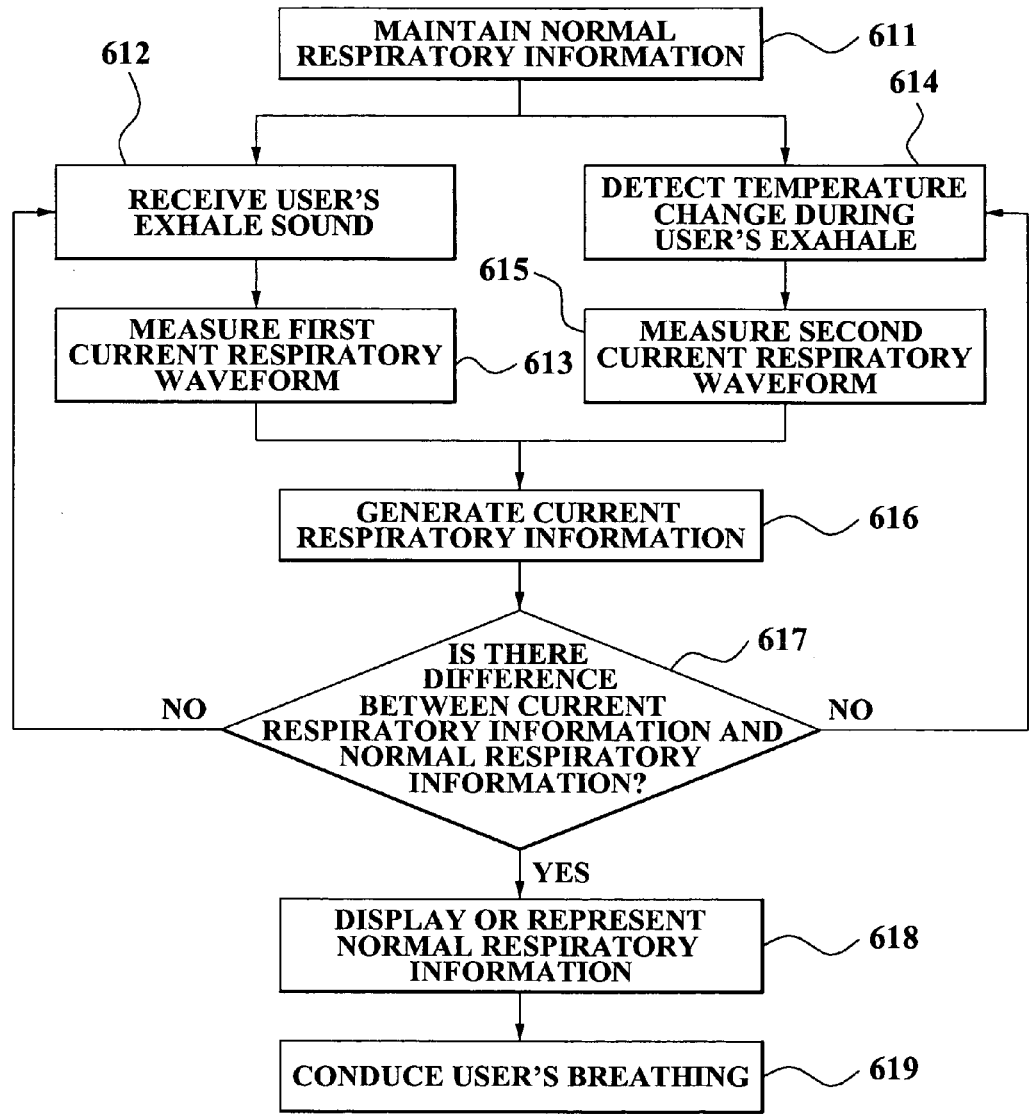

SYSTEM, MEDIUM, AND METHOD TO CONDUCE A USER'S BREATHING

CROSS-REFERENCE TO RELATED APPLICATIONS

This application claims priority from Korean Patent Application No. 10-2006-0001104, filed on Jan. 4, 2006, in the Korean Intellectual Property Office, the entire disclosure of which is incorporated herein by reference.

BACKGROUND OF THE INVENTION

1. Field of the Invention

Embodiments of the present invention relate at least to a system, medium, and method to guide/conduce a user's breathing. More particularly, such a system, medium, and method may detect a user's exhaling sound signal and/or an ambient temperature change during breathing, and then generate respiratory information from analyzing such sensor data. If this respiratory information is different from normal respiratory information of the user, e.g., at a normal non-stressed state, a user may be presented with information to help adjust his or her breathing to be closer to the normal non-stressed state.

2. Description of the Related Art

As ubiquitous-related technologies have recently been highlighted, the ubiquitous technology field using portable terminals has also been advancing every day. Particularly, a Ubiquitous (U)-Health Care has recently been in the spotlight as a remarkable technology field owing to a recent health craze and "well-being" phenomenon among people. Ubiquitous (U)-Health Care refers to a ubiquitous technology in which chips or sensors associated with a medical service are installed at various living spaces of the human being so that all the people can be naturally provided with medical services anytime and anywhere. According to such a Ubiquitous Health Care, health care in hospitals including various kinds of health diagnoses, disease management, emergency management, consultation with a doctor, etc., can be naturally implemented in each person's daily life without having to actually visit the hospital.

A causal link has been found between some diseases and stress, e.g., stress generated by people's busy daily lives. In almost all these cases, people breathe more rapidly and irregularly as compared to their normal breathing habits. In this case, they may attempt to modify their breathing to conform to a normal respiratory cycle or take deep breaths so that only their parasympathetic nerves are activated, so as to conduce psychological stability, and thereby reduce stress.

As such, since stress derives from various sources, normal respiration is very important for prevention and reduction of stress. In this regard, the inventors have found that there is a need for a portable system that may measure a user's respiratory state, determine whether the user may be under stress based on the user's respiratory state, and then help conduce stable normal breathing if necessary, as the part of the Ubiquitous Health Care.

SUMMARY OF THE INVENTION

To overcome the above problems, an aspect of an embodiment of the present invention is to provide a system, medium, and method for conducing a user to modify their breathing, where a user's current respiratory information is determined based on his or her exhale sound and/or a sensed ambient temperature change occurring during his or her exhale. When the current respiratory information is different from normal respiratory information of the user, at a normal state, the normal breathing respiratory information may be provided to the user so that the user can simply and easily measure and correct their own respiratory state anytime and anywhere, e.g., through a portable system which he or she can always carry around.

Still another aspect of an embodiment of the present invention is to provide a portable system, medium, and method for conducing a user to modify their breathing, where a user's normal respiratory information is displayed or represented to him or her through a predetermined display or audio output. The user can simply and easily correct their own respiratory state to maintain psychological stability anytime and anywhere, e.g., through such a portable system which he or she can always carry around.

Additional aspects and/or advantages of the invention will be set forth in part in the description which follows and, in part, will be apparent from the description, or may be learned by practice of the invention.

To achieve the above and/or other aspects and advantages, embodiments of the present invention include a system for conducing a user's breathing, including a breathing monitoring device to detect a user's breathing, a respiratory information generator to generate current respiratory information of the user based on the user's breathing, with the current respiratory information including a current respiratory cycle and/or current respiratory rate of the user, and a breathing-conducing unit to compare the current respiratory information with predefined respiratory information of the user, and to display and/or represent the predefined respiratory information to the user through a display and/or audio output if the current respiratory information and the predefined respiratory information are different, wherein, when the current respiratory information and the predefined respiratory information are different, the respiratory information generator continues to review the user's breathing while the predefined respiratory information is displayed and/or represented to the user through the display and/or audio output, and wherein the breathing-conducing unit further provides visual and/or audio feedback to the user to indicate a progression of the user's breathing in matching the predefined respiratory information.

The system may include a memory to store the predefined respiratory information, the predefined respiratory information being a normal respiratory cycle and/or normal respiratory rate of the user, with the normal respiratory cycle and/or normal respiratory rate representing a breathing state of the user that does not indicate stress.

Here, the normal respiratory cycle and normal respiratory rate may be previously generated by the respiratory information generator.

Further, the breathing monitoring device may be a microphone to detect a sound generated and/or a temperature sensor to detect an ambient temperature change during an exhale.

Further, the system may be a portable device. In addition, the portable device may include at least one of a mobile communication terminal, a personal digital assistant (PDA), a handheld gaming device, an MP3 player, a PMP (Portable Multimedia Player), a digital multimedia broadcasting (DMB) terminal, and a notebook computer.

A period of the user's breathing may be determined to be an exhale period based on a magnitude of the user's breathing being greater than a predetermined threshold value, wherein a period of the user's breathing during which the magnitude of the user's breathing is not greater than the predetermined threshold value may be determined to be an inhale period of the user's breathing, and wherein the comparison of the current respiratory information with the predefined respiratory information by the respiratory information generator may be based on the exhale period and the inhale period.

The predetermined threshold may represent a change in a detected ambient temperature and/or a detected sound level.

In addition, the respiratory information generator may add the exhale period and the inhaled period to calculate the current respiratory cycle, divide the exhale period by the inhale period to calculate the current respiratory rate, and use the current respiratory cycle and/or the current respiratory rate in the comparison of the current respiratory information with the predefined respiratory information.

Further, the breathing-conducing unit may display and/or represent detected exhale information and/or detected inhale information of the user's breathing in the providing of the visual and/or audio feedback to the user through the display and/or the audio output together with predefined exhale information and/or predefined inhale information of the predefined respiratory information.

To achieve the above and/or other aspects and advantages, embodiments of the present invention include a method of conducing a user's breathing, the method may include detecting a user's breathing, generating a current respiratory information of the user based on the user's breathing, with the current respiratory information including a current respiratory cycle and/or current respiratory rate of the user, and comparing the current respiratory information with predefined respiratory information of the user, and displaying and/or representing the predefined respiratory information to the user through a display and/or an audio output if the current respiratory information and/or the predefined respiratory information are different, wherein, when the current respiratory information and the predefined respiratory information are different, the generating of the current respiratory information continues while the predefined respiratory information is displayed and/or represented to the user through the display and/or audio output, and wherein the comparing of the current respiratory information further includes providing visual and/or audio feedback to the user to indicate a progression of the user's breathing in matching the predefined respiratory information.

The method may include maintaining the predefined respiratory information in a memory, the predefined respiratory information being a normal respiratory cycle and/or normal respiratory rate of the user, with the normal respiratory cycle and/or normal respiratory rate representing a breathing state of the user that does not indicate stress.

Further, the normal respiratory cycle and normal respiratory rate may be previously generated by the generating of the current respiratory information when the user's breathing was the breathing state of the user that does not indicate stress.

The detecting of the user's breathing may further be performed by detecting an audible aspect of the user's breathing and/or by detecting an ambient temperature change during an exhale.

The comparing of the current respiratory information, the displaying and/or representing of the predefined respiratory information to the user, and providing of visual and/or audio feedback to the user may be performed by a portable device includes at least one of a mobile communication terminal, a personal digital assistant (PDA), a handheld gaming device, an MP3 player, a PMP (Portable Multimedia Player), a digital multimedia broadcasting (DMB) terminal, and a notebook computer.

Further, a period of the user's breathing may be determined to be an exhale period based on a magnitude of the user's breathing being greater than a predetermined threshold value, wherein a period of the user's breathing during which the magnitude of the user's breathing is not greater than the predetermined threshold value is determined to be an inhale period of the user's breathing, and wherein the comparison of the current respiratory information with the predefined respiratory information is based on the exhale period and the inhale period.

The predetermined threshold may represent a change in a detected ambient temperature and/or a detected sound level.

In addition, the method may further include adding the exhale period and the inhaled period to calculate the current respiratory cycle, dividing the exhale period by the inhale period to calculate the current respiratory rate, and using the current respiratory cycle and/or the current respiratory rate in the comparison of the current respiratory information with the predefined respiratory information.

Still further, the method may include displaying and/or representing detected exhale information and/or detected inhale information of the detected user's breathing in the providing of the visual and/or audio feedback to the user through the display and/or the audio output together with predefined exhale information and/or predefined inhale information of the predefined respiratory information.

To achieve the above and/or other aspects and advantages, embodiments of the present invention include at least one medium including computer readable code to implement embodiments of the present invention.

BRIEF DESCRIPTION OF THE DRAWINGS

These and/or other aspects and advantages of the invention will become apparent and more readily appreciated from the following description of the embodiments, taken in conjunction with the accompanying drawings of which:

FIG. 6 illustrates a process for conducing a user to modify their breathing using a portable system, according to an embodiment of the present invention.

DETAILED DESCRIPTION OF THE PREFERRED EMBODIMENTS

Figure 1:
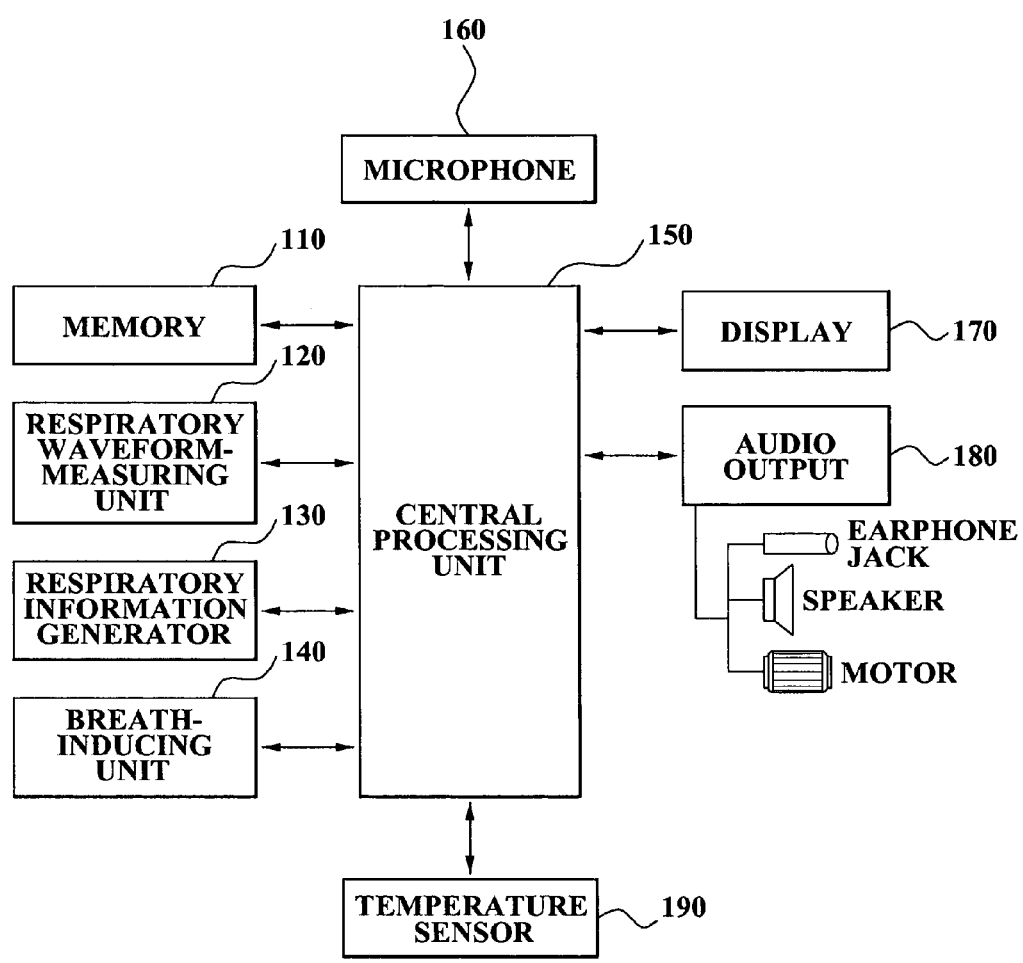
FIG. 1 illustrates a system for conducing a user's normal breathing, according to an embodiment of the present invention.

Reference will now be made in detail to embodiments of the present invention, examples of which are illustrated in the accompanying drawings, wherein like reference numerals refer to the like elements throughout. Embodiments are described below in order to explain the present invention by referring to the figures.

According to an embodiment of the present invention, a system for conducing a user's normal breathing may include a microphone(s), temperature sensor(s), display(s), or audio output(s), which may together, or individually, be embodied in portable terminals, such as a personal digital assistant (PDA), a cellular phone, a personal communication service (PCS) phone, a hand-held PC, a CDMA-2000 (1X, 3X) phone, a wideband CDMA (WCDMA) phone, a dual band/dual mode phone, a global standard for mobile communications (GSM) phone, a mobile broadband system (MBS) phone, a digital multimedia broadcasting (DMB) phone, an MP3 player, a notebook computer, a handheld gaming device, a personal media player (PMP), and a navigation terminal, for example. Here, alternative embodiments are equally available.

FIG. 1 illustrates a system/device for conducing a user's normal breathing, according to an embodiment of the present invention.

Referring to FIG. 1, the system may include a memory 110, a respiratory waveform-measuring unit 120, a respiratory information generator 130, a breathing-conducing unit 140, a central processing unit (CPU) 150, a microphone 160, a display 170, an audio output 180 and a temperature sensor 190, for example. In embodiments of the present invention, the system may be a portable system, and in addition, may include only the microphone 160, only the temperature sensor 190, a combination of the two, or such sampling aspects may be accomplished through alternative elements.

In an embodiment, the memory 110 may store normal respiratory information of a user, with the normal respiratory information including the user's respiratory cycle or respiratory rate at a normal state, for example.

The memory 110 may be include any of a USB memory of various capacities, a CF memory, an SD memory, a mini SD memory, an XD memory, a memory stick, a memory stick duo, an SMC memory, an MMC memory, and an RS-MMC, for example, noting that alternatives are equally available. Similarly, the memory 110 may be of an internal type included in an inner construction of a corresponding portable element of the system/device, or an external type disposed remote from such a portable system/device. Again, the memory 110 may support the above-mentioned memory types as well as any type of memory that is likely to be developed and appear in the near future, such as phase change random access memories (PRAMs), ferroelectric random access memories (FRAMs), and magnetic random access memories (MRAMs), for example.

The microphone 160 may receive a sound generated during the user's exhale. Generally, one's breath includes a short, almost explosive expiration (or exhale) and a slightly longer inspiration (inhale) following the expiration.

Thus observance of the exhale sound can be usually be made during the user's exhale, e.g., by sampling by microphone 160. Here, it is noted that sounds are not usually made by the user during the user's inhale, which also, or in the alternative, could be used as a delineation between the user's inhaling and exhaling of air.

Figure 2:
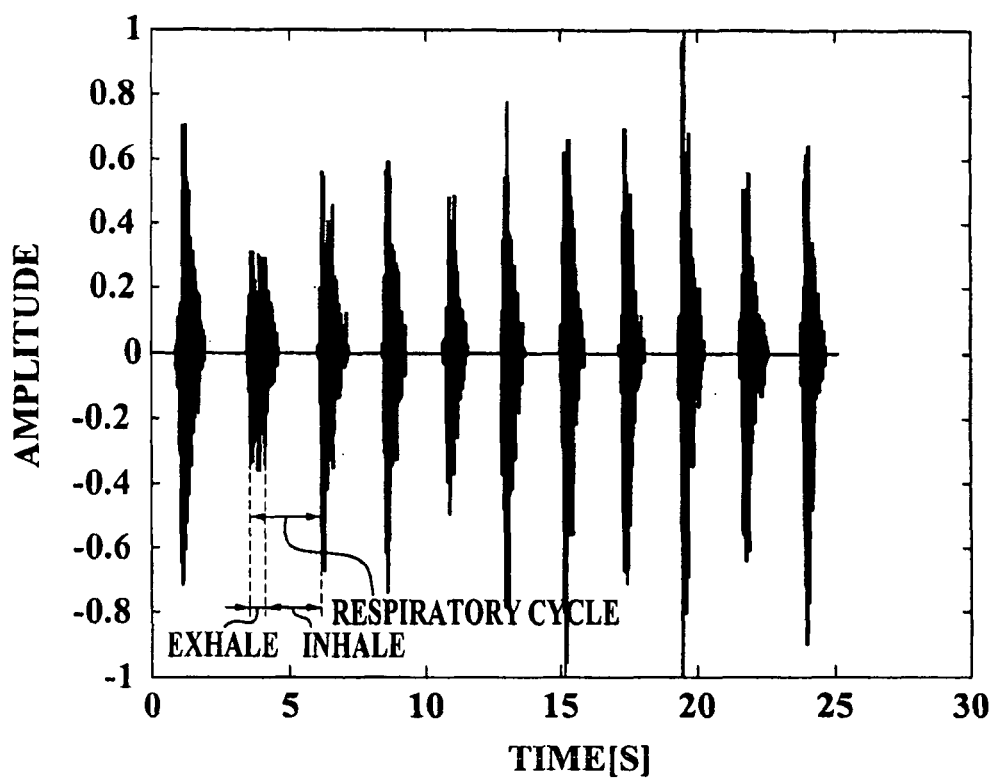
FIG. 2 illustrates a measured current respiratory waveform, according to an embodiment of the present invention.

The respiratory waveform-measuring unit 120 may receive a first current respiratory waveform of the user based on the user's exhale sound, e.g., as sampled for a certain period of time. Thus, the respiratory waveform-measuring unit 120 may receive the first current respiratory waveform of the user, according to the user's exhale sound, as received by the microphone 160, noting that alternative embodiments are equally available. An example of the first current respiratory waveform is illustrated in FIG. 2, where the signal illustrates an exhale period and an inhale period. That is, during the exhale period, the waveform has the amplitude of more than a predetermined threshold value and can be measured. Conversely, during the inhale period, little or no sound may be generated or detected.

The temperature sensor 190 may also sense an ambient temperature change occurring during the user's exhale. Usually, the ambient temperature changes due to a convection phenomenon of air during the user's respiration. Thus, in an embodiment, the temperature sensor 190 may sense the ambient temperature change occurring during a user's exhale.

Figure 3:
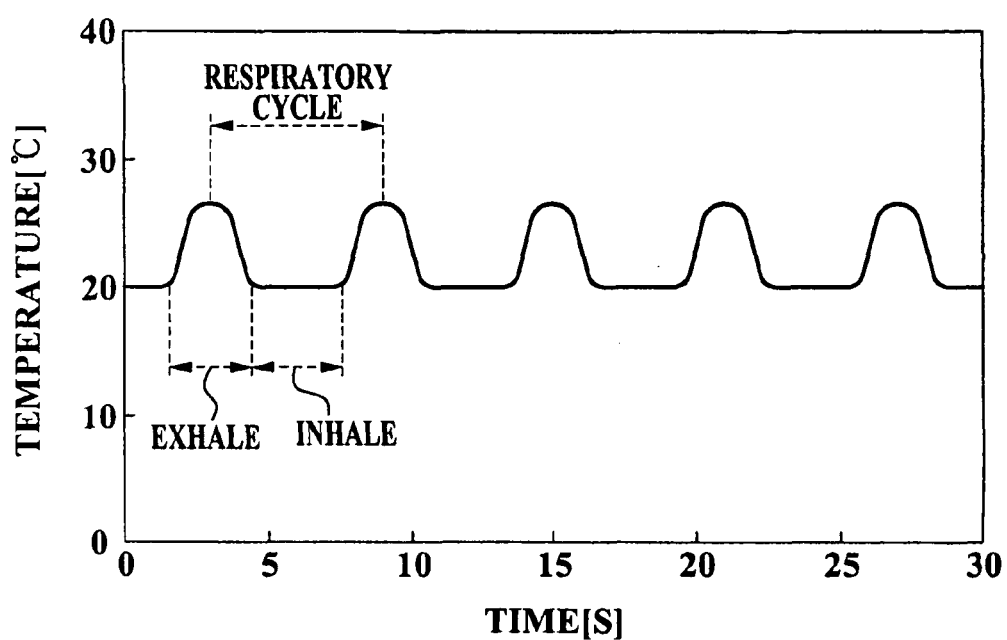
FIG. 3 illustrates another measured current respiratory waveform, according to an embodiment of the present invention.

Accordingly, the respiratory waveform-measuring unit 120 may measure a second current respiratory waveform of the user, e.g., based on the ambient temperature change sensed for a certain period of time. The second current respiratory waveform illustrated in FIG. 3 includes an exhale period and an inhale period. That is, as illustrated in FIG. 3, the measured ambient temperature changes during the exhale period and reverts back to the original temperature during the inhale period. Here, the period during which the ambient temperature changes may be recognized as the exhale period. Since the ambient temperature does not change during the inhale period, the period during which the ambient temperature does not change thus may be recognized as the inhale period.

Thus, the respiratory information generator 130 may generate both a normal and a current respiratory information, e.g., based on the measured first current respiratory waveform and/or the measured second current respiratory waveform of the user. As an example, the generating of the user's current respiratory information based on the first current respiratory waveform will now be described. The same techniques are equally applicable to the second current respiratory waveform.

As illustrated in FIG. 2, the respiratory information generator 130 may determine the period during which the magnitude of the waveform is greater than a predetermined threshold value, among respective periods of the first current respiratory waveform, as an exhale period of the user. Similarly, the respiratory information generator 130 may further determine the period during which the magnitude of the waveform is smaller than the predetermined threshold value as an inhale period of the user, for example.

With this approach, it is possible eliminate or minimize the affect of noise, e.g., from other sources nearby the user, that may be picked up by the microphone 110 along with the user's exhale sound.

Accordingly, in an embodiment, the respiratory information generator 130 may then generate a graph indicative of the current respiratory information of the user. The current respiratory information graph could also be interpreted as a conversion of the first current respiratory waveform into a digital signal or digital information. Alternatively, the input from the microphone could already be digitized, in which case the conversion of the same to a graph form may still be implemented. In an embodiment, the digital signal of current respiratory information of the graph may include information for both the exhale period and an inhale period of the user. Such techniques can equally be applied to the use of the temperature sensor and the second current respiratory waveform to either implement embodiments of the present invention with either technique, or both together. The current respiratory information may represent the current respiratory cycle or the current respiratory rate of the user, for example.

Figure 4:
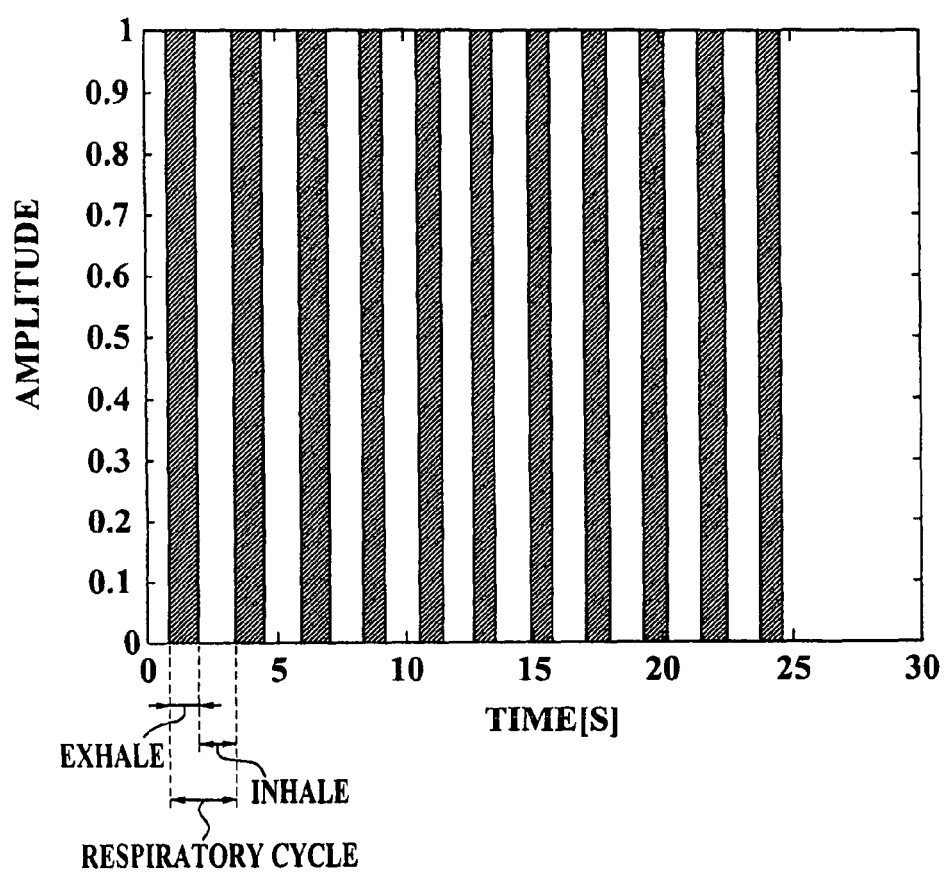
FIG. 4 illustrates generated current respiratory information, according to an embodiment of the present invention.

The respiratory cycle will be discussed as meaning a value obtained by adding an inhale time to an exhale time, though embodiments are not limited thereto. Similarly, the respiratory rate will be discussed as meaning a value obtained by dividing the exhale time by the inhale time, for example. Accordingly, using FIG. 4 as only an example, it can be seen that the current respiratory cycle can be implemented with the addition of the exhale period and the inhale period in a specific respiratory period. Further, the current respiratory rate can also be implemented by a division of the exhale period by the inhale period in the specific respiratory period.

The breathing-conducing unit 140 may then compare the generated current respiratory information with the previously detected, known, or expected normal respiratory information, e.g., stored in the memory 110. For example, the breathing-conducing unit 140 may compare the current respiratory cycle or the current respiratory rate with the normal respiratory cycle or the normal respiratory rate, respectively.

In an embodiment where the normal respiratory information is also detected, to compare between the current respiratory information and the normal respiratory information, the respiratory waveform-measuring unit 120 may measure the user's normal respiratory waveform, and the respiratory information generator 130 may generate the user's normal respiratory information based on the normal respiratory waveform. The generated normal respiratory information of the user may then be stored in the memory 110. As an example, the measurement of the normal respiratory waveform and the generation of the normal respiratory information may be implemented in the same manner as that of the current respiratory waveform and that of the current respiratory information, as described above.

The breathing-conducing unit 140 may control the display of the normal respiratory information to the user through a certain display 170 of a system/device, e.g., if the current respiratory information and the normal respiratory information are different from each other as a result of the comparison. Alternatively, or in addition, the breathing-conducing unit 140 may provide the normal respiratory information to the user through an audio output 180 of the system.

For example, the breathing-conducing unit 140 may control the display of a normal exhale time and/or a normal inhale time according to the normal respiratory information through the display 170 and/or the audio output 180, which will be described in more detail below with reference to FIGS. 5A and 5B.

Figure 5A:
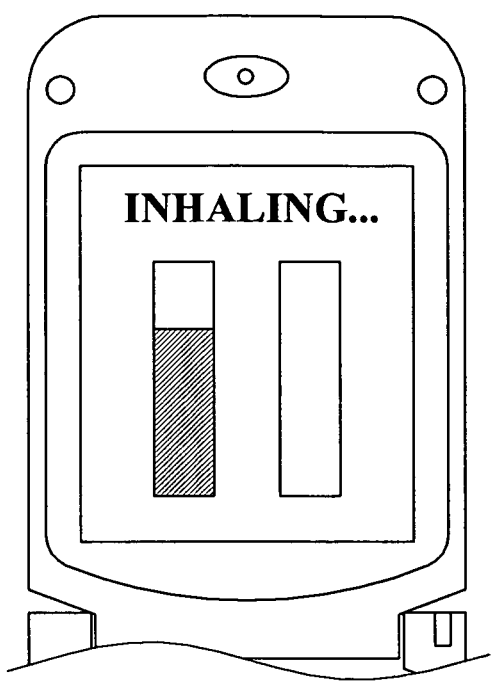
FIGS. 5A and 5B respectively illustrate a user's normal respiratory information displayed on a display of a portable system and a breathing screen provided to a user based on the normal respiratory information, according to an embodiment of the present invention.
Figure 5B:
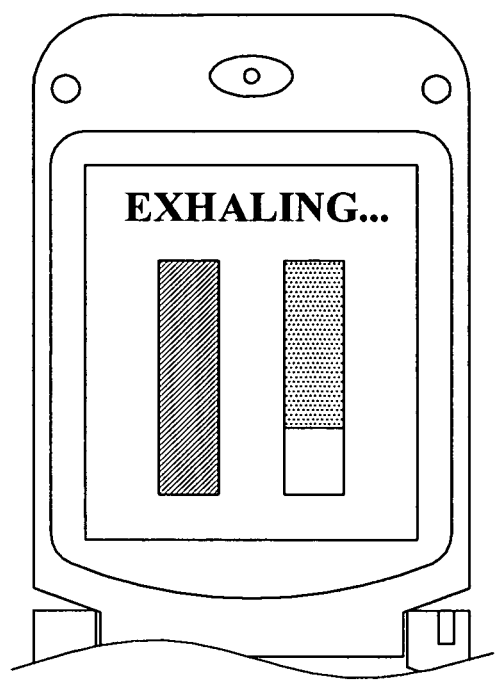

FIGS. 5A and 5B illustrate a user's normal respiratory information being displayed on a display of a portable terminal/device, e.g., on an LCD screen of the portable terminal/device, according to an embodiment of the present invention.

FIG. 5A illustrates a bar graph for guiding an inhale breath according to the normal inhale timing of the user. That is, here in this embodiment, the height of the bar graph represents the time needed for the user's normal inhale breath.

In addition, as the breathing is provided to the user, when he or she inhales air, a illustrated gauge can be displayed on the bar graph alongside the illustrated normal inhalation information. Therefore, the user can be guided through their inhale breath until the illustrated inhale breath gauge fully fills the bar graph, to thereby conduce the normal breathing of the user. Here, the illustrated gauge is shown aside the normal inhalation information. However, embodiments are not limited thereto, e.g., the illustrated gauge could be illustrated as overlaying the normal inhalation information, or illustrated alone without the normal inhalation information.

FIG. 5B illustrates a bar graph for guiding an exhale breath, e.g., according to the normal exhale timing of the user. Similarly, it is possible to conduce the user to exhale with a normal breath in the same manner as the above inhale breath technique. In case of the inhale breath and the exhale breath, the speed in which the gauge of each bar graph fills may change differently depending on each case. In addition, though the inhale breath and exhale bar graphs are illustrated as being displayed separately, they could also be illustrated together. Alternative embodiments are equally available. In addition, alternate illustrating techniques are equally available.

Thus, when the user breathes more rapidly and/or more irregular than the user's normal breathing habit, for example, e.g., due to stress, the desired normal breathing, according to the normal respiratory information, may be provided the user so that his or her parasympathetic nerves are activated so as to ensure the user's psychological stability, for example.

Referring back to FIG. 1, the central processing unit (CPU) 150 may typically include a processor to process the data of the inventive device/system. Here, according to an embodiment where all illustrated elements are enclosed within a single portable device, the central processing unit (CPU) 150 may control the operation of the memory 110, the respiratory waveform-measuring unit 120, the respiratory information generator 130, the breathing-conducing unit 140, the microphone 160, the display 170, the audio output 180 and the temperature sensor 190, for example. To this end, the central processing unit (CPU) 150 may also implement an incorporated/attached mobile station modem (MSM), digital signal processor (DSP), open multimedia application platform (OMAP), etc. In addition, in alternative embodiments the illustrated system of FIG. 1 may be embodied in different devices, or a mixture of the same.

In addition, the display 170 may include a certain screen to display the current respiratory information and/or the normal respiratory information. Respiratory information in addition to the normal respiratory information may also be available, in differing embodiments of the present invention. In other words, the display 170 may include any of a super twisted nematic (STN) LCD, a thin film transistor (TFT) LCD, an organic electroluminescent (EL) LCD, a cathode ray tube (CRT), a plasma display panel (PDP), etc., for example, noting that alternative embodiments are equally available.

In addition, the audio output 180, which may output various sounds generated from the portable device, may include any of a speaker, an earphone jack, a microphone jack, and a vibration motor, for example. In differing embodiments, the audio output 180 may further output the current respiratory information and/or the normal respiratory information, or another type of respiratory information, in a certain audio format to provide the breath information or guidance to the user.

FIG. 6 illustrates a process for conducing a user's breathing, according to an embodiment of the present invention.

According to this embodiment of the present invention, the system may maintain a user's predetermined respiratory information of a normal state, e.g., in a memory, or may obtain the same from an alternate source, in operation 611. At this time, the normal respiratory information may include the user's normal respiratory cycle or normal respiratory rate. As noted above, embodiments of the present invention are not limited to the application of the normal respiratory cycle or normal respiratory rate, as other respiratory cycles or other respiratory rates may be available.

A sound, for example, generated during the user's exhale may be monitored, in operation 612, and a first current respiratory waveform of the user may be measured, in operation 613. The system may also, or in the alternative, sense an ambient temperature change occurring during the user's exhale, in operation 614, and measure a second current respiratory waveform of the user, in operation 615.

The system may generate the user's current respiratory information, based on the measured first current respiratory waveform and/or the measured second current respiratory waveform, in operation 616. The current respiratory information may further include a current respiratory cycle and/or a current respiratory rate of the user.

The system may compare the current respiratory information with the normal respiratory information, for example, in operation 617, and if it is determined, in operation 617, that the current respiratory information and the normal respiratory information are similar or identical to each other, the process may return to operations 612 or 614, where the system may repeatedly receive the sound and/or temperature information.

However, if it is determined, in operation 617, that the current respiratory information and the normal respiratory information are different, the process may proceed to operation 618, where the system may display or represent the normal respiratory information to the user through any of a display and/or audio output, for example.

The system may, thus, then conduce the breathing of the user based on the normal respiratory information with the display and/or representation of the normal respiratory information, in operation 619, thereby helping the user activate his or her parasympathetic nerves according to the normal breath state, so as to ensure his or her psychological stability. In operation 619, the system, according to a present invention, may be implemented to conduce the breathing of the user for a predetermined period of time to thereby alleviate stress of the user, and may further be implemented in a measurement mode for measuring the respiratory cycle of the user again after the conducing of the breathing of the user for the predetermined time period to thereby identify whether or not the respiratory cycle of the user has returned to a normal state.

In addition to the above described embodiments, embodiments of the present invention can also be implemented through computer readable code/instructions in/on a medium, e.g., a computer readable medium. The medium can correspond to any medium/media permitting the storing and/or transmission of the computer readable code.

The computer readable code can be recorded/transferred on a medium in a variety of ways, with examples of the medium including magnetic storage media (e.g., ROM, floppy disks, hard disks, etc.), optical recording media (e.g., CD-ROMs, or DVDs), and storage/transmission media such as carrier waves, as well as through the Internet, for example. Here, the medium may further be a signal, such as a resultant signal or bitstream, according to embodiments of the present invention. The media may also be a distributed network, so that the computer readable code is stored/transferred and executed in a distributed fashion.

According to an embodiment of the present invention, a system, medium, and method conducing a user's breathing has an advantageous effect in that a user's current respiratory information may be produced from his or her respiratory waveform, based on his or her exhale sound and/or a change in ambient temperature caused by the user's exhale, and when the current respiratory information is different from the normal respiratory information of the user, a normal breathing may be provided to the user so that the user can simply and easily measure and correct their own respiratory state anytime. The user's normal respiratory information may be displayed or represented through a display or audio output, for example. Further, as noted above, the recited system may also be embodied in a portable device, or a system where all or some of the elements are portable, e.g., such that the monitoring and conducing of the breathing of the user can be accomplished anywhere and anytime, e.g., through a portable device which the user can always be carried around.

Although a few embodiments of the present invention have been shown and described, the present invention is not limited to the described embodiments. Instead, it would be appreciated by those skilled in the art that changes may be made to these embodiments without departing from the principles and spirit of the invention, the scope of which is defined by the claims and their equivalents.

What is claimed is:

1. A system for conducing a user's breathing, comprising:
   a breathing monitoring device to detect a user's breathing;
   a respiratory information generator to generate current respiratory information of the user based on the user's breathing, with the current respiratory information including a current respiratory cycle and/or current respiratory rate of the user; and
   a breathing-conducing unit to compare the current respiratory information with predefined respiratory information of the user, and to display and/or represent the predefined respiratory information to the user through a display and/or audio output if the current respiratory information and the predefined respiratory information are different,
   wherein, when the current respiratory information and the predefined respiratory information are different, the respiratory information generator continues to review the user's breathing while the predefined respiratory information is displayed and/or represented to the user through the display and/or audio output,
   wherein the breathing-conducing unit further provides visual and/or audio feedback to the user to indicate a progression of the user's breathing in matching the predefined respiratory information, and
   wherein the respiratory information generator generates the current respiratory information by comparing a magnitude of the user's breathing to a predetermined threshold value and distinguishing a period of the user's breathing into an inhale period and an exhale period based on a result of the comparing of the magnitude of the user's breathing to the predetermined threshold value, and
   a first portion of the period during which the magnitude of the user's breathing is greater than the predetermined threshold value is determined to be the exhale period and a second portion of the period during which the magnitude of the user's breathing is not greater than the predetermined threshold value is determined to be the inhale period of the user's breathing.

2. The system of claim 1, further comprising a memory to store the predefined respiratory information, the predefined respiratory information being one of a normal respiratory cycle of the user, a normal respiratory rate of the user, and both the normal respiratory cycle and the normal respiratory rate of the user, with the normal respiratory cycle and normal respiratory rate representing a breathing state of the user that does not indicate stress.

3. The system of claim 2, wherein any of the normal respiratory cycle and the normal respiratory rate of the one predefined respiratory information are previously generated by the respiratory information generator.

4. The system of claim 1, wherein the breathing monitoring device is a microphone to detect a sound generated and/or a temperature sensor to detect an ambient temperature change during an exhale.

5. The system of claim 1, wherein the system is a portable device.

6. The system of claim 5, wherein the portable device includes at least one of a mobile communication terminal, a personal digital assistant (PDA), a handheld gaming device, an MP3 player, a PMP (Portable Multimedia Player), a digital multimedia broadcasting (DMB) terminal, and a notebook computer.

7. The system of claim 1, wherein the predetermined threshold represents a change in a detected ambient temperature and/or a detected sound level.

8. The system of claim 1, wherein the respiratory information generator adds the exhale period and the inhale period to calculate the current respiratory cycle, divides the exhale period by the inhale period to calculate the current respiratory rate, and uses the current respiratory cycle and/or the current respiratory rate in the comparison of the current respiratory information with the predefined respiratory information.

9. The system of claim 1, wherein the breathing-conducing unit displays and/or represents detected exhale information and/or detected inhale information of the user's breathing in the providing of the visual and/or audio feedback to the user through the display and/or the audio output together with predefined exhale information and/or predefined inhale information of the predefined respiratory information.

10. A non-transitory computer-readable storage medium comprising an executable program that when executed by at least one processing device controls the at least one processing device to control a performance of a method of conducing a user's breathing, the method comprising:
  detecting a user's breathing;
  generating a current respiratory information of the user based on the user's breathing, with the current respiratory information including a current respiratory cycle and/or current respiratory rate of the user; and
  comparing the current respiratory information with predefined respiratory information of the user, and displaying and/or representing the predefined respiratory information to the user through a display and/or an audio output if the current respiratory information and the predefined respiratory information are different,
  wherein, when the current respiratory information and the predefined respiratory information are different, the generating of the current respiratory information continues while the predefined respiratory information is displayed and/or represented to the user through the display and/or audio output,
  wherein the comparing of the current respiratory information further comprises providing visual and/or audio feedback to the user to indicate a progression of the user's breathing in matching the predefined respiratory information, and
  wherein the generating of the current respiratory information comprises generating the current respiratory information by comparing a magnitude of the user's breathing to a predetermined threshold value and accordingly distinguishing a period of the user's breathing into an inhale period and an exhale period based on a result of the comparing of the magnitude of the user's breathing to the predetermined threshold value, and
  a first portion of the period during which the magnitude of the user's breathing is greater than the predetermined threshold value is determined to be the exhale period and a second portion of the period during which the magnitude of the user's breathing is not greater than the predetermined threshold value is determined to be the inhale period of the user's breathing.

11. A system for conducing a user's breathing, comprising:
  a breathing monitoring device to detect a user's breathing;
  a respiratory information generator to generate current respiratory information of the user based on detected inhale and exhale periods of the user's breathing, with the current respiratory information including a calculated current respiratory cycle and/or current respiratory rate of the user, respectively calculated based on both the detected inhale period and the detected exhale period; and
  a breathing-conducing unit to compare the current respiratory information with predefined respiratory information of the user, with the predefined respiratory information being one of a predefined respiratory cycle of the user, a predefined respiratory rate of the user, and both the predefined respiratory cycle and the predefined respiratory rate of the user,
  wherein the respiratory information generator is configured to display and/or represent to the user the predefined respiratory information, by providing visual and/or audio feedback to the user to indicate a progression of the user's breathing in matching the predefined respiratory information based on a result of the comparing of the current respiratory information with the predefined respiratory information,
  the respiratory information generator detects the inhale period and the exhale period of the user's breathing based on a comparison of a magnitude of the user's breathing to a predetermined threshold value, and
  a first portion of the period during which the magnitude of the user's breathing is greater than the predetermined threshold value is determined to be the exhale period and a second portion of the period during which the magnitude of the user's breathing is not greater than the predetermined threshold value is determined to be the inhale period of the user's breathing.

12. The system of claim 11, wherein the respiratory information generator adds the exhale period and the inhale period to calculate the current respiratory cycle, divides the exhale period by the inhale period to calculate the current respiratory rate, and uses the current respiratory cycle and/or the current respiratory rate in the comparison of the current respiratory information with the predefined respiratory information.

13. The system of claim 11, wherein the predefined respiratory cycle and predefined respiratory rate are respectively predefined based on a previous detected breathing state of the user that does not indicate stress.

14. The system of claim 11, wherein the breathing-conducing unit displays and/or represents the detected exhale period and/or the detected inhale period of the user's breathing in the providing of the visual and/or audio feedback to the user through a display and/or an audio output together with predefined exhale information and/or predefined inhale information of the predefined respiratory information.

* * * * *